(12) United States Patent
Brown et al.

(10) Patent No.: US 9,355,218 B2
(45) Date of Patent: May 31, 2016

(54) SECURE MEDICATION TRANSPORT AND ADMINISTRATION SYSTEM

(75) Inventors: Barry Arthur Brown, Encinitas, CA (US); Duane E. Veach, Wichita, KS (US); James David DeFreece, Olathe, KS (US)

(73) Assignee: CareFusion 303, Inc., San Diego, CA (US)

( * ) Notice: Subject to any disclaimer, the term of this patent is extended or adjusted under 35 U.S.C. 154(b) by 278 days.

(21) Appl. No.: 11/928,745

(22) Filed: Oct. 30, 2007

(65) Prior Publication Data
US 2009/0108016 A1    Apr. 30, 2009

(51) Int. Cl.
| | |
|---|---|
| *G06F 17/00* | (2006.01) |
| *G06F 19/00* | (2011.01) |
| *B65D 83/04* | (2006.01) |
| *G07F 11/62* | (2006.01) |
| *G07F 17/00* | (2006.01) |
| *A61J 7/00* | (2006.01) |

(52) U.S. Cl.
CPC ........... *G06F 19/3462* (2013.01); *A61J 7/0084* (2013.01); *G07F 11/62* (2013.01); *G07F 17/0092* (2013.01); *A61J 7/0069* (2013.01)

(58) Field of Classification Search
CPC ...... A61J 7/0069; A61J 7/0076; A61J 7/0084
USPC .................................................. 700/231–244
See application file for complete search history.

(56) References Cited

U.S. PATENT DOCUMENTS

| | | | |
|---|---|---|---|
| 4,847,764 A * | 7/1989 | Halvorson | .................... 700/231 |
| 5,314,243 A | 5/1994 | McDonald et al. | |
| 5,408,443 A * | 4/1995 | Weinberger | .................... 368/10 |

(Continued)

FOREIGN PATENT DOCUMENTS

| | | |
|---|---|---|
| EP | 1 310 900 A2 | 5/2003 |
| EP | 1310900 A2 | 5/2003 |

(Continued)

OTHER PUBLICATIONS

PCT International Search Report/Written Opinion for International Application No. PCT/US2008/081592 dated Feb. 18, 2009.

(Continued)

*Primary Examiner* — Michael K Collins
(74) *Attorney, Agent, or Firm* — McDermott Will & Emery LLP

(57) ABSTRACT

A portable medication dispensing system is described. In some embodiments, the system includes a portable medication tote comprising a securable compartment configured to hold medication, and a controller, responsive to access information, configured to assign a patient to the securable compartment such that medications for the patient are authorized for placement into the securable compartment. The controller is also configured to selectively permit a user access to the medications for the patient in the securable compartment when the access information indicates the user has access to the securable compartment, and restrict access to retrieval of the medications for the patient in the securable compartment when the access information indicates the user does not have access to the securable compartment. The system also includes an information output module configured to output usage information regarding access to the securable compartment.

20 Claims, 10 Drawing Sheets

(56) References Cited

U.S. PATENT DOCUMENTS

| | | | |
|---|---|---|---|
| 5,661,978 A * | 9/1997 | Holmes et al. | 62/3.6 |
| 5,905,653 A | 5/1999 | Higham et al. | |
| 5,945,651 A * | 8/1999 | Chorosinski et al. | 235/375 |
| 6,032,155 A * | 2/2000 | de la Huerga | |
| 6,116,461 A * | 9/2000 | Broadfield et al. | 221/98 |
| 6,138,865 A | 10/2000 | Gilmore | |
| 6,169,707 B1 * | 1/2001 | Newland | 368/10 |
| 6,219,587 B1 | 4/2001 | Ahlin et al. | |
| 6,338,007 B1 * | 1/2002 | Broadfield et al. | 700/231 |
| 6,529,446 B1 * | 3/2003 | de la Huerga | 368/10 |
| 6,532,399 B2 | 3/2003 | Mase | |
| 6,604,019 B2 | 8/2003 | Ahlin et al. | |
| 6,609,047 B1 | 8/2003 | Lipps | |
| 6,611,733 B1 * | 8/2003 | De La Huerga | 700/236 |
| 6,636,780 B1 | 10/2003 | Haitin et al. | |
| 6,640,159 B2 * | 10/2003 | Holmes et al. | 700/244 |
| 6,658,322 B1 | 12/2003 | Frederick et al. | |
| 6,707,381 B1 * | 3/2004 | Maloney | 340/568.1 |
| 6,785,589 B2 | 8/2004 | Eggenberger et al. | |
| 6,788,997 B1 | 9/2004 | Frederick | |
| 7,006,894 B2 * | 2/2006 | de la Huerga | 700/244 |
| 7,010,389 B2 * | 3/2006 | Lunak et al. | 700/243 |
| 7,052,097 B2 * | 5/2006 | Meek et al. | 312/222 |
| 7,155,306 B2 | 12/2006 | Haitin et al. | |
| 7,216,802 B1 * | 5/2007 | De La Huerga | 235/380 |
| 7,679,520 B2 * | 3/2010 | Zerhusen | A47B 23/046 340/286.07 |
| 7,715,277 B2 * | 5/2010 | de la Huerga | 368/10 |
| 7,747,347 B2 * | 6/2010 | Park, IV | 700/243 |
| 7,809,470 B2 * | 10/2010 | Shoenfeld | 700/243 |
| 7,911,349 B2 * | 3/2011 | Zerhusen | A47B 23/046 340/286.07 |
| 8,140,187 B2 * | 3/2012 | Campbell et al. | 700/242 |
| 8,334,779 B2 * | 12/2012 | Zerhusen | A47B 23/046 340/286.07 |
| 8,368,545 B2 * | 2/2013 | Zerhusen | A47B 23/046 340/286.07 |
| 8,674,839 B2 * | 3/2014 | Zerhusen | A47B 23/046 340/286.07 |
| 2001/0002448 A1 * | 5/2001 | Wilson et al. | 700/233 |
| 2003/0052787 A1 * | 3/2003 | Zerhusen | A47B 23/046 340/573.1 |
| 2003/0099158 A1 * | 5/2003 | De la Huerga | 368/10 |
| 2003/0120384 A1 | 6/2003 | Haitin et al. | |
| 2004/0046020 A1 * | 3/2004 | Andreasson et al. | 235/385 |
| 2004/0054436 A1 | 3/2004 | Haitin et al. | |
| 2004/0148055 A1 | 7/2004 | Shoenfeld | |
| 2006/0125356 A1 | 6/2006 | Meek, Jr. et al. | |
| 2007/0078562 A1 * | 4/2007 | Park, IV | 700/243 |
| 2007/0088461 A1 * | 4/2007 | Haitin et al. | 700/241 |
| 2008/0319581 A1 * | 12/2008 | Vahlberg et al. | 700/242 |

FOREIGN PATENT DOCUMENTS

| | | |
|---|---|---|
| JP | 2002-516228 A | 6/2002 |
| JP | 2009-518133 A | 5/2009 |
| WO | WO-9826746 A2 | 6/1998 |
| WO | WO-99/60982 A2 | 12/1999 |
| WO | WO-0032073 A1 | 6/2000 |
| WO | WO-2007035185 A2 | 3/2007 |
| WO | WO-2007/070312 A1 | 6/2007 |
| WO | WO-2007/081947 A2 | 7/2007 |

OTHER PUBLICATIONS

Australian Notice of Acceptance for Australiam Application No. 2008318742, dated Feb. 25, 2014, 2 pages.
Australian Patent Examination Report No. 1 for Australian Application No. 2008318742, dated Jul. 26, 2012, 3 pages.
Australian Patent Examination Report No. 2 for Australian Application No. 2008318742, dated Mar. 18, 2013, 3 pages.
Australian Patent Examination Report No. 3 for Australian Application No. 2008318742, dated Aug. 2, 2013, 3 pages.
Australian Patent Examination Report No. 4 for Australian Application No. 2008318742, dated Nov. 28, 2013, 3 pages.
Canadian Office Action for Canadian Application No. 2703758, dated Mar. 6, 2015, 4 pages.
Chinese Decision of Rejection for Chinese Application No. 200880123519.1, dated Jul. 3, 2013, 21 pages.
Chinese First Office Action for Chinese Application No. 200880123519.1, dated Mar. 22, 2012, 15 pages.
European Office Action for European Application No. 08845598, dated Nov. 23, 2011, 7 pages.
International Preliminary Report on Patentability for Interntational Application No. PCT/US2008/081592, dated May 4, 2010, 8 pages.
Japanese Notification of Reasons of Refusal for Japanese Application No. 2010-532206, dated Jan. 15, 2013, 7 pages.
New Zealand Examination Report for New Zealand Application No. 584956, dated Jul. 11, 2011, 2 pages.
Russian Decision to Grant for Russian Application No. 2010121895, dated May 15, 2013, 21 pages.
Russian Office Action for Russian Application No. 2010121895, dated Dec. 11, 2012, 29 pages.
Chinese Notification of Reexamination for Application No. 200880123519.1, dated Feb. 3, 2016, 7 pages excluding translation.
Canadian Office Action for Application No. 2703758, dated Apr. 4, 2016, 4 pages.

* cited by examiner

SECURE MEDICATION TRANSPORT AND ADMINISTRATION SYSTEM

STATEMENT AS TO RIGHTS TO INVENTIONS MADE UNDER FEDERALLY SPONSORED RESEARCH OR DEVELOPMENT

Not Applicable.

FIELD

The present disclosure generally relates to apparatus and methods for providing health care and, in particular, relates to providing care to a patient through controlled access to medication.

BACKGROUND

It is well known in the medical community, and in particular, in hospitals, to use a centralized inventory system for dispensing and administering medications. In this system, medications provided by a pharmacy, for example, are temporarily stored in a centralized area or station for administration.

Caregivers who seek to administer to patients medications from the centralized storage area often transport the medications in an unsecured fashion, such as by loading the selected medications onto a movable cart, onto a tray, or even into their own pockets. Consequently, there are provided by a pharmacy, for example, several risks associated with unsecured transport, such as the wrong type or amount of medication being administered to a patient, the medication being stolen, or the mixing of medications where the medications are temporarily stored for administration.

Furthermore, little or no record is kept of the taking or dispensing of such medications, such as the type and dose of the medication, when and by whom the medication was removed, and to whom and at what time the medication was administered. Healthcare facilities are thus often inhibited from determining if the type and amount of medication given to a patient was appropriate, or whether any medication was administered at all.

SUMMARY

Embodiments of the secure medication transport and administration system (hereinafter "secure tote") disclosed herein provide for the recorded and secure loading of patient-specific medications into a secure, portable device which records and verifies patient bedside access to the medications by an authorized caregiver.

According to one embodiment of the present disclosure, a portable medication dispensing system comprises a portable medication tote comprising at least one securable compartment configured to hold medication, and a controller responsive to access information. The controller is configured to assign a patient to the at least one securable compartment such that medications for the patient are authorized for placement into the at least one securable compartment. The controller is further configured to selectively permit a user access to the medications for the patient in the at least one securable compartment when the access information indicates the user has access to the at least one securable compartment, and restrict access to retrieval of the medications for the patient in the at least one securable compartment when the access information indicates the user does not have access to the at least one securable compartment. The system further comprises an information output module configured to output usage information regarding access to the at least one securable compartment.

According to one aspect of the present disclosure, a method for patient-specific medication dispensing comprises assigning a patient to at least one securable compartment in a portable medication tote, the at least one securable compartment configured to store medications for the patient. The method further comprises selectively permitting a user access to store the medications for the patient in the at least one securable compartment when access information indicates the user has storage access to the at least one securable compartment, and comparing a bedside identification of the user and a bedside identification of the patient to the access information to determine whether the user has access to dispense to the patient the medications for the patient in the at least one securable compartment. The method also comprises selectively permitting the user access to dispense to the patient the medications for the patient in the at least one securable compartment using the determination, and outputting usage information regarding the user access to at least one of the assignment, access, and the determination made regarding the at least one securable compartment.

According to another embodiment of the present disclosure, a computer-readable medium having computer-executable instructions for causing a processor to execute instructions to control a portable medication dispensing system by performing steps comprising assigning a patient to at least one securable compartment in a portable medication tote, the at least one securable compartment configured to store medications for the patient. The computer-readable medium further comprises computer-executable instructions for performing steps comprising selectively permitting a user access to store the medications for the patient in the at least one securable compartment when access information indicates the user has storage access to the at least one securable compartment, and comparing a bedside identification of the user and a bedside identification of the patient to the access information to determine whether the user has access to dispense to the patient the medications for the patient in the at least one securable compartment. The computer-readable medium also comprises computer-executable instructions for performing steps comprising selectively permitting the user access to dispense to the patient the medications for the patient in the at least one securable compartment using the determination, and outputting usage information regarding the user access to the assignment, access, and/or determination made regarding the at least one securable compartment.

According to a further embodiment of the present disclosure, a portable dispensing system comprises a portable item tote comprising at least one securable compartment configured to hold items, and a controller responsive to access information. The controller is configured to assign an assignee to the at least one securable compartment such that items for the assignee are authorized for placement into the at least one securable compartment. The controller is further configured to selectively permit a user access to the items for the assignee in the at least one securable compartment when the access information indicates the user has access to the at least one securable compartment, and restrict access to retrieval of the items for the assignee in the at least one securable compartment when the access information indicates the user does not have access to the at least one securable compartment. The system further comprises an information output module configured to output usage information regarding access to the at least one securable compartment.

Additional features and advantages of the invention will be set forth in the description below, and in part will be apparent from the description, or may be learned by practice of the invention. The objectives and other advantages of the invention will be realized and attained by the structure particularly pointed out in the written description and claims hereof as well as the appended drawings.

It is to be understood that both the foregoing general description and the following detailed description are exemplary and explanatory and are intended to provide further explanation of the discussed embodiments as claimed.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings.

DETAILED DESCRIPTION

In the following detailed description, numerous specific details are set forth to provide a full understanding of the present disclosure. It will be obvious, however, to one ordinarily skilled in the art that the embodiments of the present disclosure may be practiced without some of these specific details. In other instances, well-known structures and techniques have not been shown in detail not to obscure the disclosure.

Figure 1:
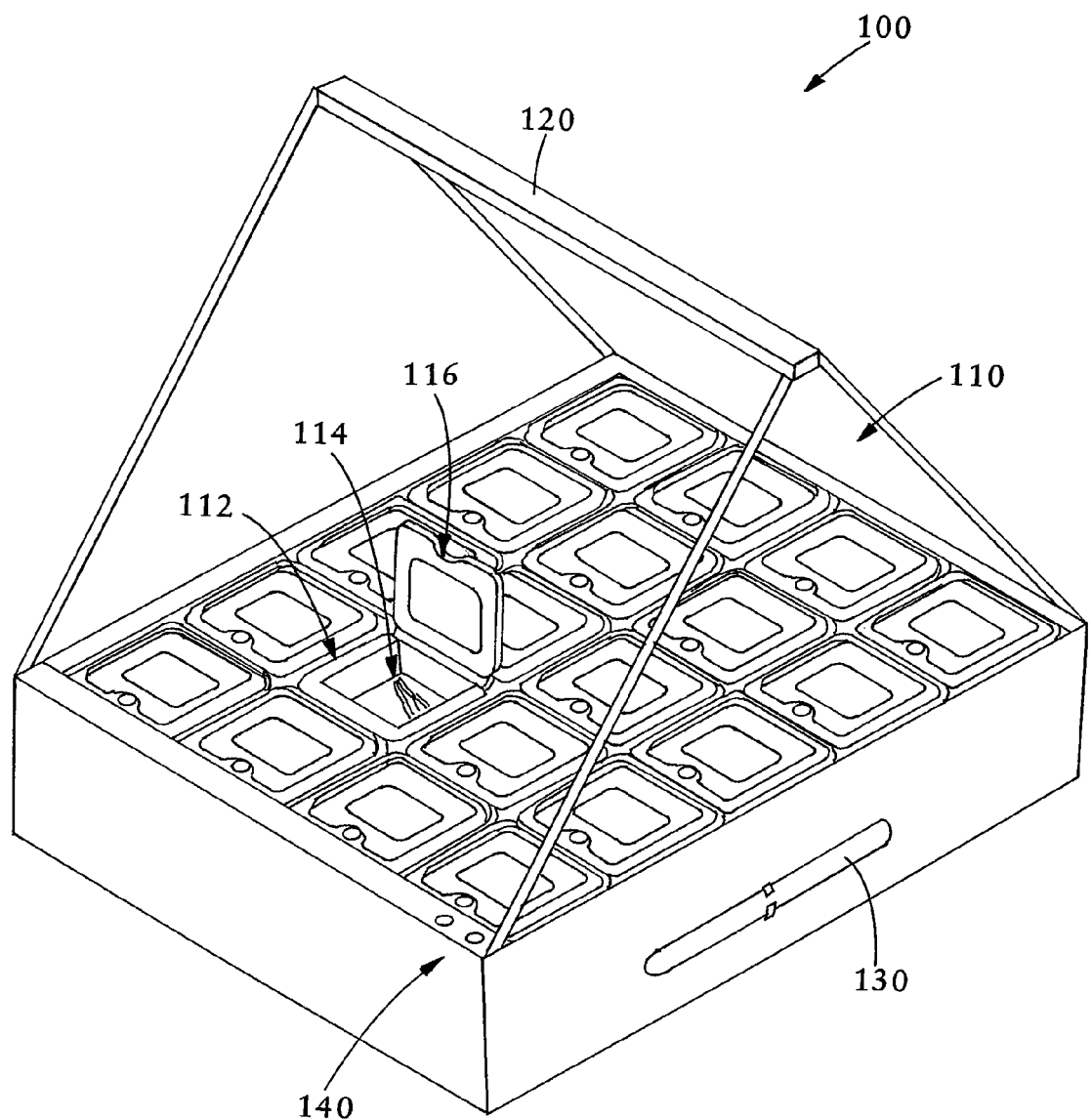
FIG. 1 illustrates one embodiment of a secure tote for secure medication transport and administration.

Referring now to the drawings, FIG. 1 illustrates one embodiment of a secure tote 100 for secure medication transport and administration. This configuration is exemplary only, such that other physical configurations may be employed.

The secure tote 100 provides secure transport for patient-specific medication from a medication storage device to a patient, where the patient-specific medications can be dispensed by a user, such as a caregiver. Through positive, physical bedside identification of both a caregiver authorized to dispense the medications from the secure tote 100 and a patient for whom those medications are intended, the secure tote 100 helps ensure that the appropriate medication type and dose is provided to the patient. The secure tote 100 is further configured to log usage information, such as access information and location information, either locally, such as in memory housed in the secure tote 100, or remotely, by transmitting the usage information to a remote information storage server. Furthermore, in certain embodiments, the secure tote 100 is configured to dock with the medication storage device, such that the secure tote 100 can directly obtain patient-specific medication information from the medication storage device when the patient-specific medication is transferred from the medication storage device to the secure tote 100.

In the embodiment illustrated in FIG. 1, the secure tote 100 comprises a plurality of securable, modular receptacles 110, a wireless barcode reader 130, a handle 120, and indicator lights 140. Each receptacle 110 itself may be a medication package that contains drugs and a package insert.

The modular receptacles 110 are configured to be moveable between a closed position and an open position, such as shown by open modular receptacle 112. Each receptacle 110 has a plurality of sidewalls that define a storage compartment as well as a top 116 that is opened and closed about a hinge. A latch assembly can be formed between top 116 and one of the sidewalls to keep top 116 in a closed position until an authorized caregiver gains access to the receptacle 110. Additional storage features, including features of exemplary modular receptacles 110, are fully disclosed in U.S. Pat. Nos. 6,116,461 and 6,338,007, which are incorporated herein by reference in their entirety. Other types of modular receptacles may be employed, however.

Each modular receptacle 110 may be used to contain various items, for example, medications 114. Each modular receptacle 110 may house multiples of one type of drug or medical supply or it may house several varieties of drugs or medical supplies. Each modular receptacle 110 may be refilled and reused many times. Each modular receptacle 110 may also include a label for identification of the contents within the receptacle, and/or some or all of top 116 may be transparent.

Although a plurality of receptacles for medication storage are illustrated in the secure tote 100 of FIG. 1, in other embodiments, other forms of storage can be used. For example, the secure tote 100 can be divided into equally accessible compartments by adjustable or fixed dividers all having a single shared, securable cover. In other embodiments, the secure tote 100 can be custom configured to match the medication and supply needs of the facility using the secure tote 100.

The secure tote 100 can be made from plastic, such as injection molded plastic, or formed from metal, and, as such, may be durable and reusable multiple times. In other embodiments, other materials can be used.

Wireless barcode reader 130 is used as an input device for receiving information such as medication information, caregiver information, and patient information. For example, wireless barcode reader 130 can be used by a caregiver to scan in patient-specific medication information when the patient-specific medication is being loaded into a modular receptacle 110, and later scan the caregiver's identification tag and a patient's identification tag at the patient's bedside in order to provide the caregiver with access to the modular receptacle 110 containing the patient's medication. By using an input device 130 such as a barcode reader, the secure tote 100 provides for rapid input of patient identification and caregiver identification information, which reduces the overall time it takes an authorized caregiver to gain access to and dispense patient-specific medications from the secure tote 100. Although wireless barcode reader 130 is illustrated, other wired or wireless input devices can be used, such as, but not limited to, a keyboard, a touch-screen display, a mouse, a microphone, a magnetic card reader, a biometric reader-sensor, a proximity reader, a radio frequency (RF) identification reader, and a symbology reader.

Output devices, such as indicator lights 140, on the exterior of the secure tote 100 are used to indicate a status of the secure tote 100. In certain embodiments, indicator lights 140 are red and green in order to provide indications for different states. For example, red indicator light 140 can be turned on if the secure tote 100 denies access to a modular receptacle 110, if the input device 110 cannot read data, if power associated with the secure tote 100 is low, or if the secure tote 100 loses communication with a network. Similarly, green indicator light 140 can be turned on if the secure tote 100 grants access to a modular receptacle 110, if the input device 110 successfully reads data, if the secure tote 100 is powered on, or if the secure tote 100 is communicating with a network.

In other embodiments, other types of output devices can be used. For example, the secure tote 100 can include audible indicators such as speakers, or other visual indicators such as display screens, including a cathode ray tube (CRT) display, vacuum fluorescent display (VFD), light emitting diode (LED) display, plasma display panel (PDP), liquid crystal display (LCD), organic light emitting diode (OLED), or surface-conduction electron-emitter display (SED).

The secure tote 100 of FIG. 1 further includes a handle 120 for ease of transport. In other embodiments, different types of handles may or may not be used depending on the needs and design of the secure tote 100. In yet further embodiments, other types of interface elements can be used.

Figure 2:
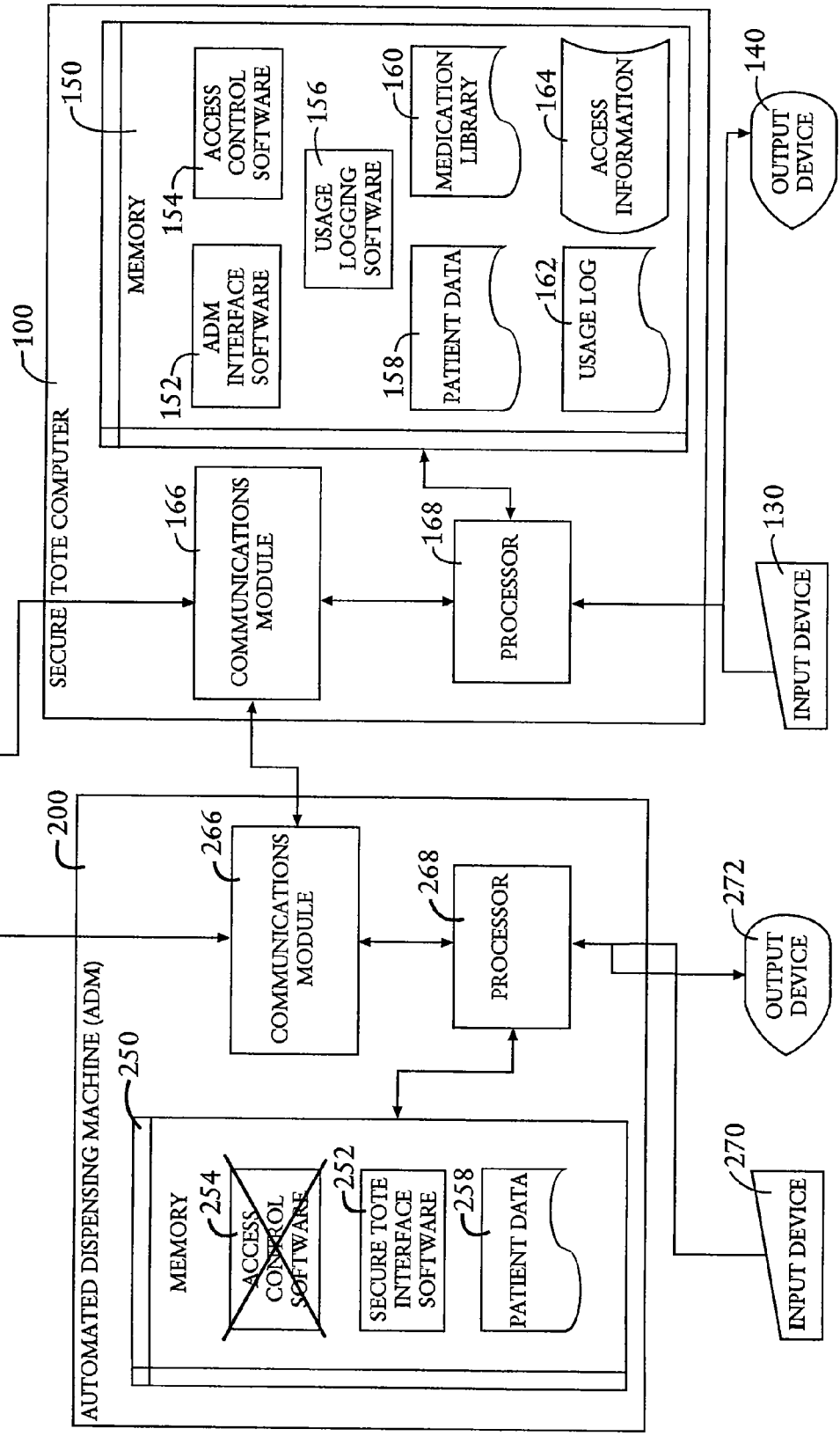
FIG. 2 is a block diagram of certain electronic features of the secure tote of FIG. 1 and of an Automated Dispensing Machine (ADM).

FIG. 2 is a block diagram of certain electronic features of the secure tote of FIG. 1 and of ADM 200. The secure tote 100 includes memory 150, communications module 166, processor 168, and, as discussed above, input device 130 and output device 140.

Processor 168, for example, a central processing unit (CPU), drives software stored in the computing device's memory 150 or elsewhere. Since the secure tote 100 is portable and, in certain embodiments, powered by a battery, the processor 168 or other circuitry may be designed for low power operation in order to provide satisfactory runtime before requiring recharging or replacement of the battery.

Communications module 166 is configured to transmit, receive, and otherwise communicate information with network 180 and/or devices on the network 180, such as ADM 200. For example, communications module 166 communicates with ADM 200 when the secure tote 100 is docked with ADM 200 through a connection between secure tote communications module 166 and ADM communications module 266. The secure tote 100 can be in continuous communication with network 180, or can connect to network 180 or another device as necessary. Communication is achieved via a communication layer that enables data transmissions. Example communications modules 166 include serial communication interfaces such as RS-232, Ethernet, Universal Serial Bus (USB), and wireless interfaces such as RF, infrared, Bluetooth® and IEEE 802.11x. For example, the secure tote 100 can be networked by connecting to a central data network device via data cables when the secure tote 100 is docked. In embodiments using communications module 266 configured for location tracking, such as by using RF technology, an additional level of security is provided by allowing for the location of the secure tote 100 to be tracked. Consequently, in such embodiments, if the secure tote 100 leaves an authorized usage area, communications module 266 can transmit an appropriate alert, and secure tote output device 140 can likewise signal an appropriate alert.

In certain embodiments, the secure tote 100 may also be "dumb," i.e., without on-board intelligence, and information about its contents may be contained within a barcode, for example, placed on the secure tote 100. In such embodiments, a receiving area of an apparatus, for example on or in ADM 200, may acquire the necessary information through scanning of the barcode on the secure tote 100 to enable ADM 200 to obtain sufficient information about the contents of the secure tote 100. The receiving area may be a drawer in ADM 200 having either an on-board computer processor 268 or a connection 266 to one remote therefrom. In yet other embodiments, the secure tote 100 can further reduce the amount of on-board intelligence, such as by suspending or even removing communication functionality. For example, the secure tote 100 can act independently, limiting or removing the need for communication with other devices or networks, while at the same time maintaining the access control and usage logging functionality discussed below.

In another embodiment, the secure tote 100 may have limited on-board intelligence. For example, the information storage device or the barcode label on the secure tote 100 may contain information about one or many modular receptacles 110, such as a receptacle number (e.g., #1234567). This preprogrammed information would typically be entered when a modular receptacle 110 is filled. In this embodiment, a human-readable label (not a barcode label) or marking on the receptacle 110 itself with the receptacle number may be used and the caregiver may, for recording purposes, manually enter the receptacle number into the computer having the preprogrammed information about the contents of the modular receptacles 110 in the secure tote 100.

The secure tote 100 also features onboard memory 150. In the embodiment illustrated, the memory 150 includes ADM interface software 152, access control software 154, usage logging software 156, patient data 158, medication library 160, usage log 162, and access information 164. Onboard memory 150 can be either non-volatile storage (e.g., read-only memory, flash memory, magnetic media, etc.), volatile storage (e.g., random-access memory), or both.

Access control software 154, which in combination with the processor 168 can jointly be referred to as a controller, is responsible for controlling access to the secure tote 100. Access control software 154 references access information 164 stored in memory 150 when authenticating a caregiver or other user attempting to use the secure tote 100. Access control software 154 may authenticate users by reference to a password, keycard, or other authentication method known to those of skill in the art. For example, access control software 154 can require the input of the appropriate patient identification and caregiver identification before unlocking a modular receptacle assigned to the caregiver and the patient containing medications for the patient. By providing verifiable access to only the appropriate medications for a patient (i.e., by opening only the correct modular receptacle), the secure tote 100 reduces the risk that a caregiver will administer the incorrect medication to a patient.

Secure tote memory 150 includes ADM interface software 152 configured to facilitate docking and communication with ADM 200 or other similarly configured devices. ADM interface software 152 is configured to communicate with various types of ADMs, so as to facilitate information transfer between ADM 200 and the secure tote 100. Similarly, in certain embodiments, secure tote interface software 252 can be loaded into the memory 250 of ADM 200 to facilitate docking between the secure tote 100 and the ADM 200.

Patient data 158 contains information concerning the contents of the secure tote 100, such as the contents of each receptacle 110. For example, patient data 158 can include assignment information for each receptacle 110 of the secure tote 100, including, but not limited to: an assigned patient, including patient-related information; an assigned caregiver authorized to fill the receptacle; an assigned caregiver authorized to dispense medications from the receptacle to the patient; medications in the receptacle, including information on the type, dose, and expiration date; authorized locations for use; the time at which the secure tote 100 was filled; and the time at which the secure tote medications 100 were dispensed.

Secure tote patient data 158 can be configured directly using a suitable input device 130 and output device 140 for the secure tote 100. For example, a specific modular receptacle can be programmed with patient, caregiver, and medication information by scanning barcodes associated with the patient, caregiver, medication, and modular receptacle using a barcode reader input device 130. A successful assignment may be indicated by flashing green indicator light 140. Appropriate barcodes may be available at or near the ADM, such as in a catalog. Individually barcoded medications can be scanned directly using the barcode reader 140.

In another embodiment, patient data 158 can be configured and downloaded from an ADM 200 to which the secure tote 100 is docked, providing for an integrated workflow between the secure tote 100 and ADM 200. For example, when a caregiver docks the secure tote 100 to ADM 200, as schematically illustrated in FIG. 2, the caregiver may assign patients and medications to various modular receptacles 110 in the secure tote 100 using ADM 200, and, thereafter, the assignment information and other information may be downloaded as patient data 258 from ADM memory 250 through ADM communications module 266 and secure tote communications module 166, and stored as patient data 158 in secure tote memory 150. As another example, pre-loaded modular receptacles 110 each containing associated patient data in memory may be available at ADM 200, and, when the modular receptacles 110 are connected to the secure tote 100, the associated patient data can be transferred from each modular receptacle 110 to the secure tote 100.

Medication library 160 stores a wide variety of information related to medications. For example, medication library 160 can include data from the Hearst Corporation's National Drug Data File, such as information on expiration dates, lot numbers, NDC numbers, types of drug or medical supply dosage, sizes of packages, numbers of items in the packages, etc. Medication library 160 can also include other information related to medications, such as the prescribing indicators (PI).

Usage logging software 156 can store transactional or other use information about the secure tote 100 in usage log 162. For example, each time a caregiver provides user input, the input is logged in usage log 162. Each time a medication is transferred to the secure tote 100, selected, and/or dispensed, the filling, selection, and/or dispensing of the medication is likewise logged in usage log 162. Similarly, the patient, medication, and caregiver assignments for the secure tote 100, such as for each modular receptacle 110, is recorded in usage log 162. Each time the secure tote 100 is docked, undocked, or otherwise connected to another device or network, the information is logged in usage log 162. For each and any transaction using the secure tote 100, usage log 162 records information, including time information, such as the times at which the secure tote 100 has been docked, filled, dispensed, put into service, taken out of service, or otherwise used. In this manner, administrators can access a detailed usage log 162 for the secure tote 100, such as for auditing purposes. Furthermore, by configuring the secure tote 100 to communicate with other devices (such as ADM 200) capable of recording transaction data, a "closed-loop" tracking of medication is provided up until the medication is administered to a patient.

Usage log 162 may be displayed locally on the secure tote 100 through a suitable output device 140 and with appropriate authorization using a suitable input device 130. Usage log 162 may be displayed remotely from the secure tote 100, when, for example, a caregiver or other authorized user interacts with a device having access to usage log 162, whether through docking or over network 180. In certain embodiments, the access control software 154 also includes code for allowing access to the usage log 162 by authorized users, who may authenticate access using a password, keycard, or other authentication method known to those of skill in the art. In certain embodiments, usage data is stored in real-time (i.e., immediately), while in other embodiments usage data is stored following a delay.

Figure 3:
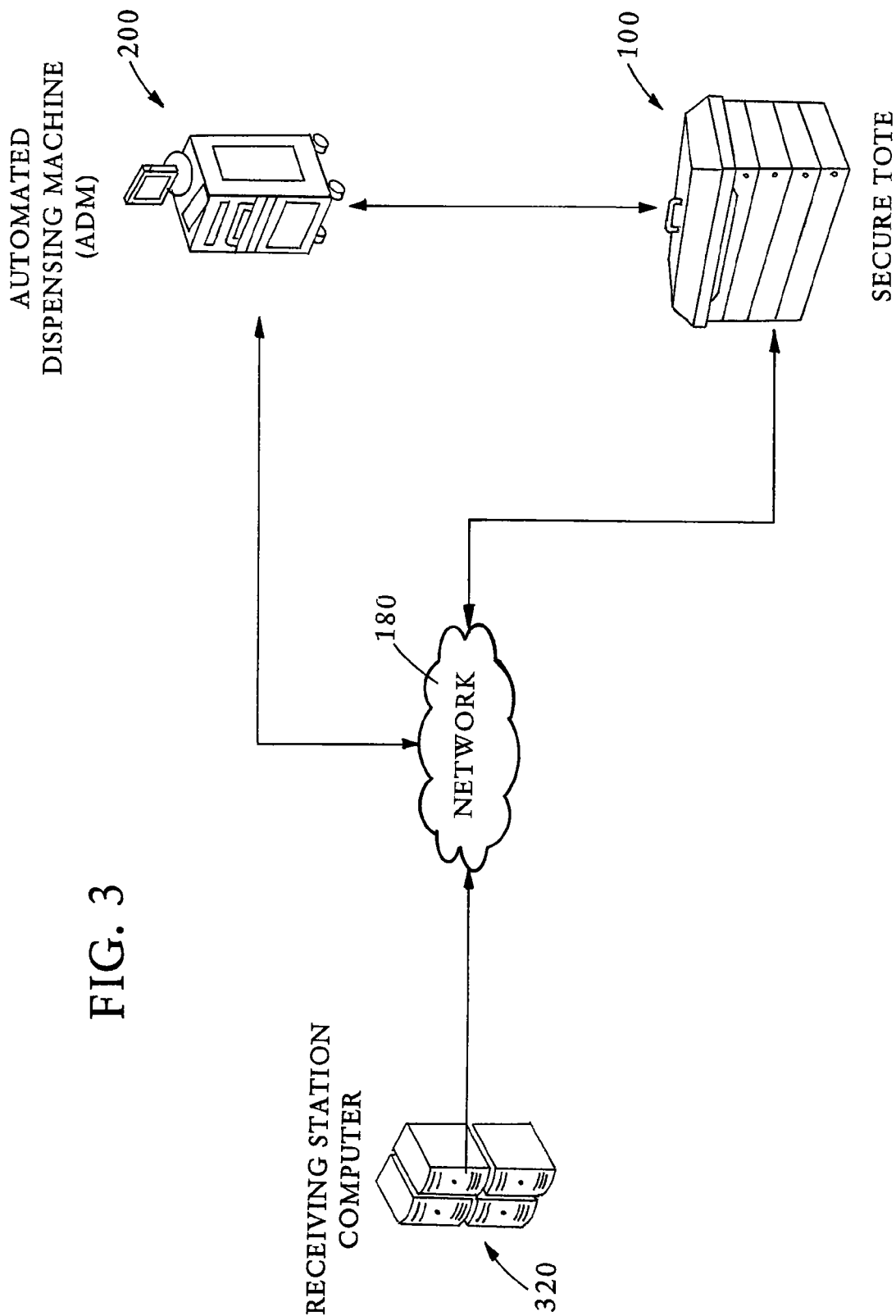
FIG. 3 is a block diagram of a network configuration for the secure tote of FIG. 1.

In certain embodiments, transactional or other use information usually stored in usage log 162 may instead be transmitted by usage logging software 156 to a central receiving station computer 320 for storage, as illustrated in FIG. 3. The information is transmitted via a network connection 180. In other embodiments, usage logging software 156 stores usage log information both locally, in usage log 162 of secure tote memory 150, as well as remotely, in receiving station computer 320. In yet further embodiments, usage logging software 156 can store usage log 162 locally, and, upon docking with a suitable device or with network 180, upload usage log 162 accordingly. Note that the physical configuration of the secure tote 100 in FIG. 3 is different from that of FIG. 1, illustrating that the physical configuration depicted in the figures is exemplary only.

In certain embodiments, the secure tote 100 can also dock to or otherwise connect to a device at a patient bedside, such as a device including a bedside information gateway. The caregiver can then interact with the bedside information gateway in order to access or configure the secure tote 100 at the patient bedside, for example, to facilitate dispensing medications from the secure tote 100 to the patient or to reconfigure the secure tote 100 based on new information made available to the caregiver when at the patient's bedside. Usage logging software 156 can optionally upload stored usage log 162 to the bedside device in order to update receiving station computer 320 with the latest usage information.

Figure 4:
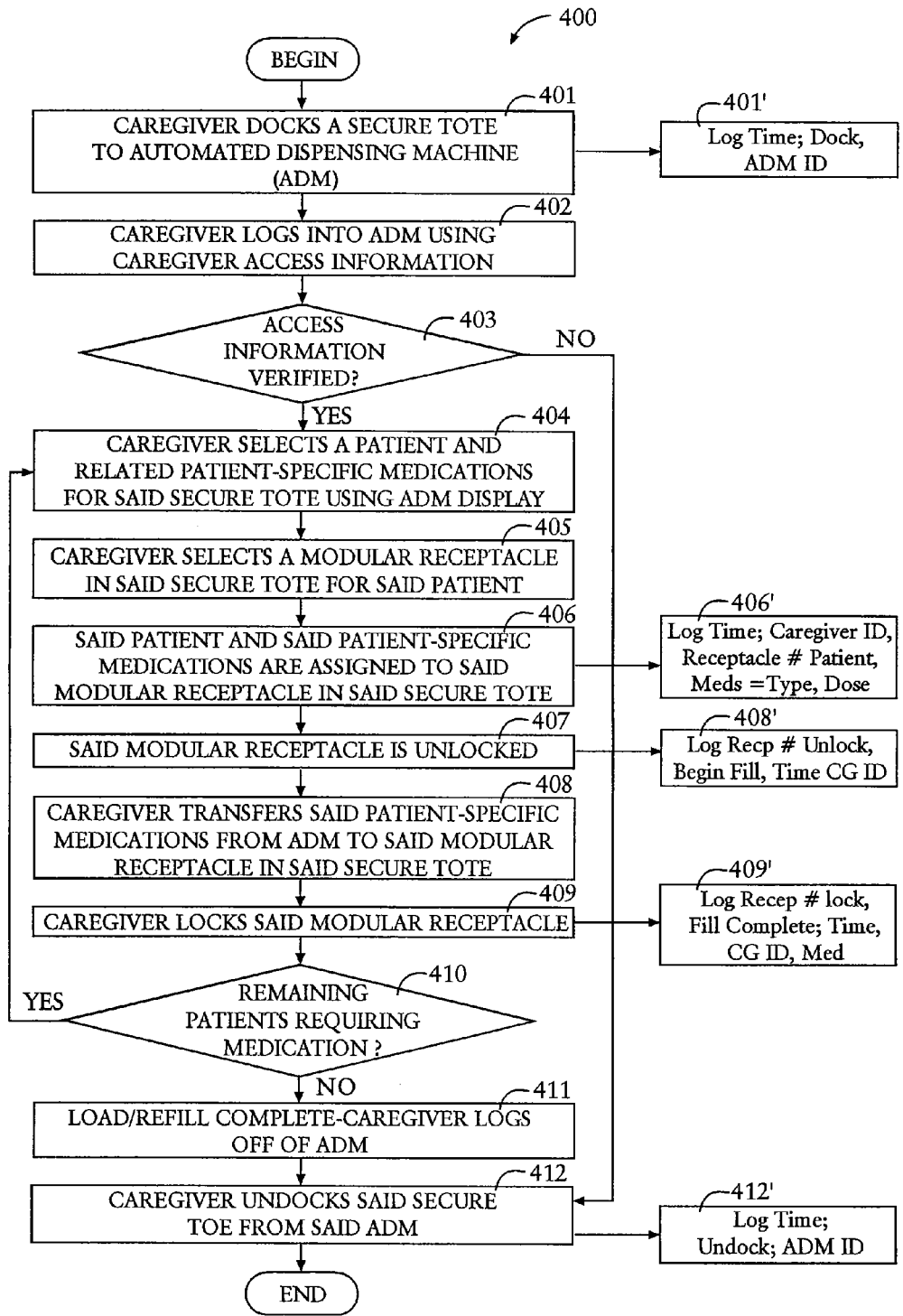
FIG. 4 is a flow diagram illustrating an exemplary process for filling medications in the secure tote of FIG. 1.

FIG. 4 is a flow diagram illustrating a process 400 for filling (or refilling) medications in the secure tote 100 of FIG. 1. Recording by usage logging software 156 for various states is reflected in similarly numbered prime (') states, as discussed below.

The process begins by moving to state 401, wherein a user, such as a caregiver, docks a secure tote 100 to ADM 200. This transaction is recorded by usage logging software 156 in state 401'. Upon docking the secure tote 100 to ADM 200, the caregiver provides access information to ADM 200 in state 402 for security purposes, so as to ensure authorized use of the secure tote 100. If the access information is verified in decision state 403, the process 400 continues to state 404. If, however, the access information is not verified, the process 400 jumps to the end state.

In state 404, the caregiver selects a patient and associated patient-specific medications to assign to a modular receptacle 110 in the secure tote 100. The caregiver in state 405 then selects the modular receptacle 110 to which to assign the patient's medications. The patient, patient-specific medications, and authorization for the caregiver are all then assigned to the selected modular receptacle 110 in state 406. Usage logging software 156 in state 406' appropriately records the assignment by recording the time at which the assignment occurred, the caregiver identification, the patient information, the patient-specific medication information, including type and dose, and the modular receptacle identification. In state 407, the assigned modular receptacle is unlocked, and recorded accordingly in state 407' by recording information such as the unlocked receptacle's identification, the time, the caregiver identification, and the action of unlocking to fill the modular receptacle with the patient-specific medication. With the modular receptacle unlocked, the caregiver can proceed to load the patient-specific medications into the assigned modular receptacle in state 408. After the medications are loaded, the caregiver locks the modular receptacle in state 409, and usage logging software 156 records the time, caregiver identification, patient-specific medication information, the modular receptacle identification, and the action of locking after a fill was completed, in state 409'. The caregiver decides in decision state 410 whether any remaining patients need to be assigned to the secure tote 100; if patients do remain, the process 400 returns to state 404, but if patients do not remain, the process proceeds to state 411.

In state 411, with loading completed, the caregiver logs off of ADM 200. The secure tote 100 is then undocked from ADM 200 in state 412, and usage logging software 156 records the time, ADM identification, and action of undocking accordingly in state 412'.

In certain embodiments, certain states of process 400 can change in order. For example, in certain embodiments, states 408 and 409 can succeed state 410, such that the caregiver can load all assigned modular receptacles at the same time. Furthermore, in certain embodiments, other types of information can be logged by usage logging software 156.

Figure 5:
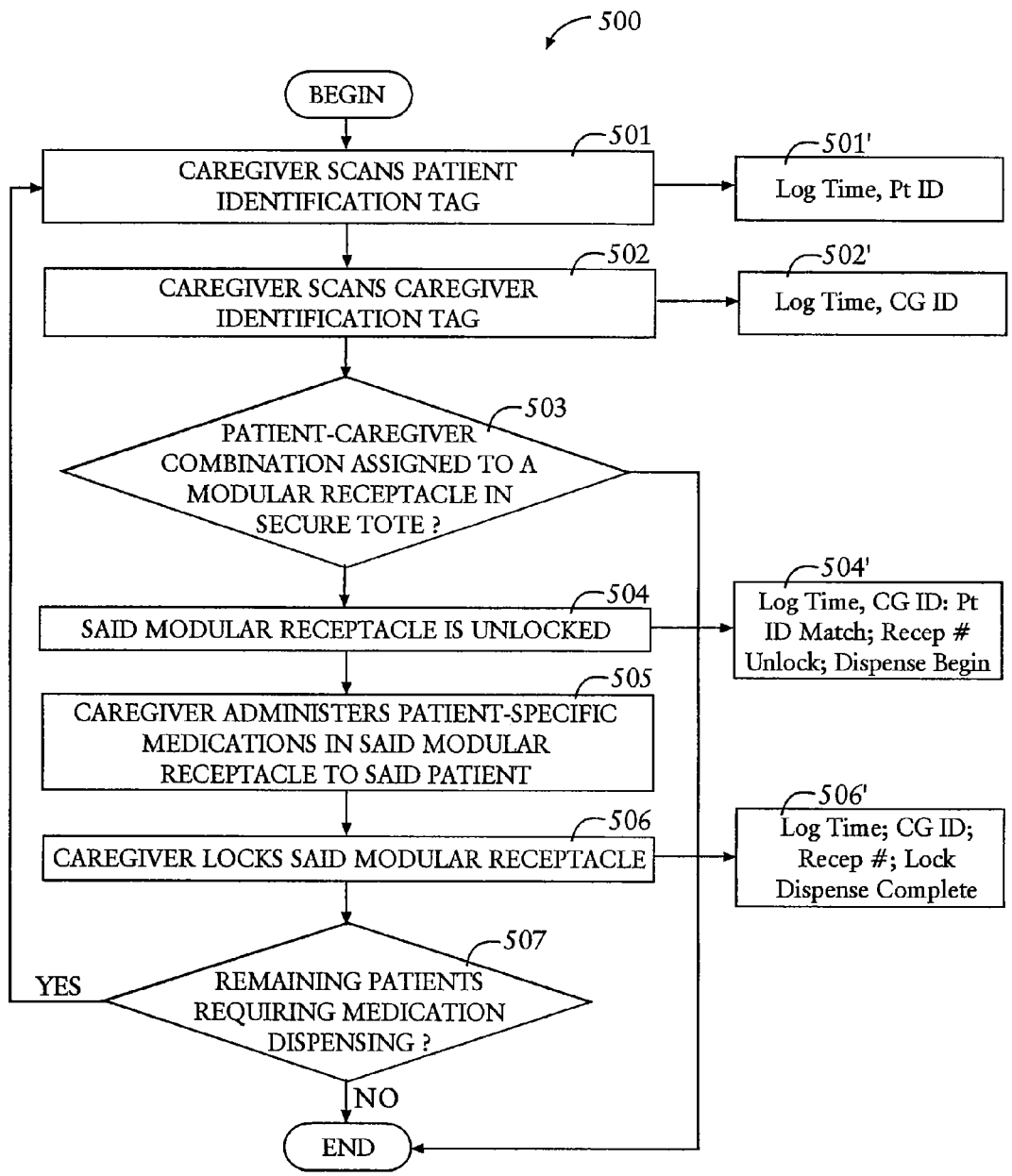
FIG. 5 is a flow diagram illustrating an exemplary process for dispensing medications from the secure tote of FIG. 1.

FIG. 5 is a flow diagram illustrating a process 500 for dispensing medications from the secure tote 100 of FIG. 1, such as at a patient's bedside. As with FIG. 4, recording by usage logging software 156 for various states in process 500 is reflected in similarly numbered prime (') states, as discussed below.

The process begins by moving to state 501 to conduct a bedside identification. In state 501, a user, such as a caregiver, scans a patient identification tag. For example, at the patient bedside, the caregiver can detach wireless barcode reader 130 from the secure tote 100 and use wireless barcode reader 130 to scan a patients' barcode wristband containing that patient's identification information. The time and patient identification is recorded by usage logging software 156 in state 501'. The caregiver then scans his/her own identification information in state 502. For example, a caregiver can use wireless barcode reader 130 to scan the caregiver's badge, which can contain the caregiver's identification information. The time and caregiver identification is recorded by usage logging software 156 in state 502'. The process 500 then proceeds to state 503.

In situations featuring a bedside information gateway device at the patient bedside, states 501 and 502 may be replaced by docking the secure tote 100 to the bedside information gateway device and authenticating the caregiver's access to the bedside information gateway device, with relevant transactions being logged. The process 500 may then proceed as described to state 503.

Secure tote access control software 154, with reference to access information 164 stored in memory 150 of the secure tote 100, determines in decision state 503 whether the patient-caregiver pairing identified in states 401 and 402 is assigned to a modular receptacle in the secure tote 100. If such a pairing is not found (such as where the caregiver does not have authorized access to dispense medications to the patient, or if the patient is not assigned to a modular receptacle 110 in the secure tote 100), the process 500 proceeds to an end state. If, however, an appropriate patient-caregiver pairing is found to be assigned to a modular receptacle 110 of the secure tote 100, the process 500 proceeds to state 504 wherein the assigned modular receptacle 110 is unlocked. In state 504', usage logging software 156 records the identification of the unlocked receptacle, the time at which it was unlocked, the authorized pairing of the caregiver identification and patient identification for whom it was unlocked, and the purpose for which it was unlocked, i.e., so the caregiver could dispense the patient-specific medications in the modular receptacle to the patient. ADM interface software 152 can optionally retrieve updated patient, caregiver, medication, or other relevant information at this step in order to ensure that the caregiver has access to the latest information when administering medications to the patient.

The caregiver administers the patient-specific medications from the open modular receptacle to the patient in state 505. After administration, the caregiver locks the modular receptacle from which the medications were dispensed to the patient, in order to signal to the secure tote 100 that the dispensing has been completed. In certain embodiments, the caregiver can take additional action to confirm the completion of dispensation to the patient of medications from the modular receptacle, such as by scanning a barcode on the modular receptacle, or by scanning each barcode on a medication if the medications are individually barcoded. In state 506', usage logging software 156 records the identification of the locked receptacle, the time at which it was locked, the authorized pairing of the caregiver identification and patient identification by whom it was locked, and the purpose for which it was locked, i.e., upon completion of dispensation by the caregiver of patient-specific medications to the patient.

The caregiver decides in decision state 507 whether any remaining patients assigned to the secure tote 100 need to receive medication stored in the secure tote 100. If patients do remain, the process 500 returns to state 501 when the caregiver proceeds to the bedside of the next patient. If patients do not remain, the process proceeds to an end state.

Figure 6:
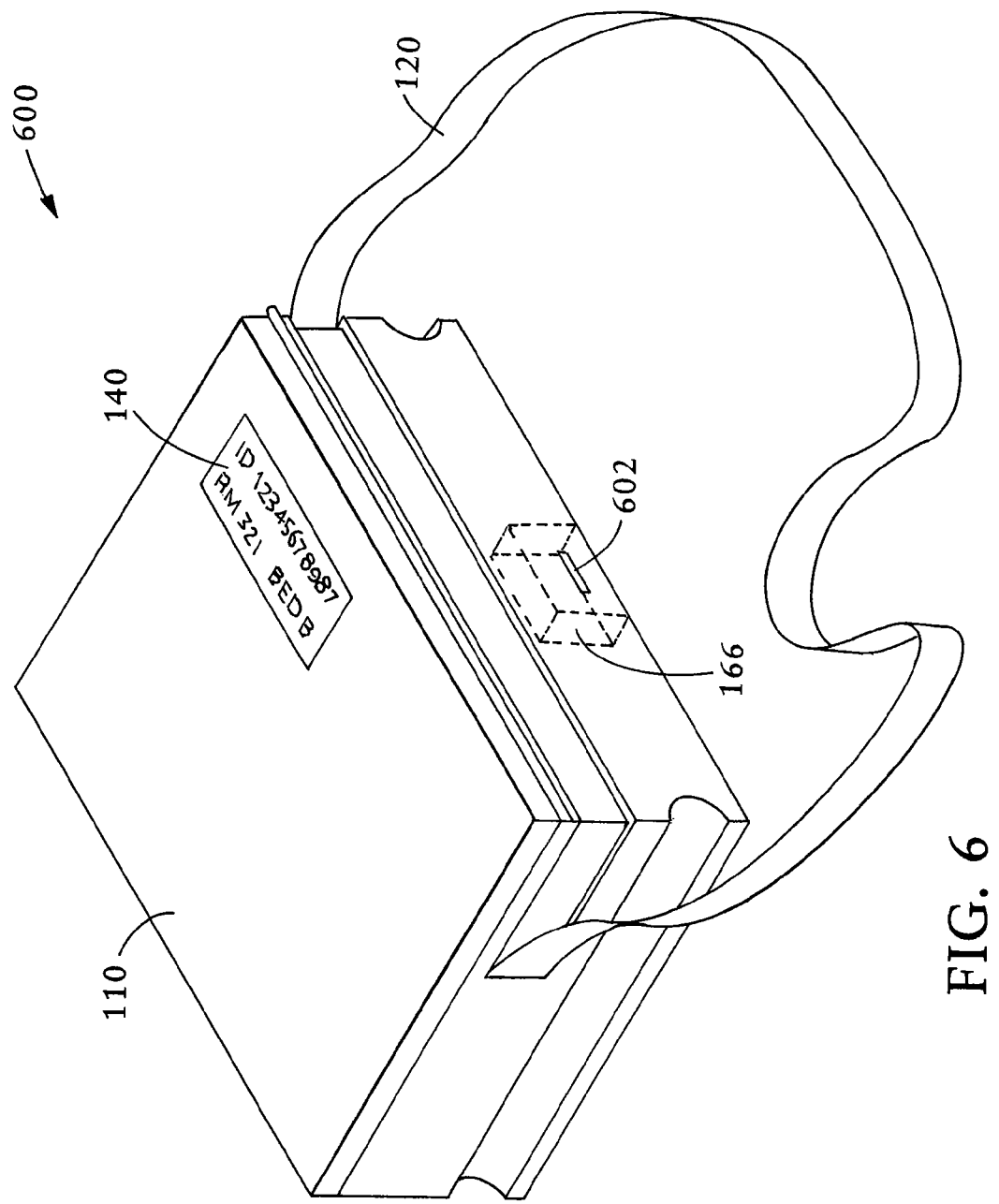
FIG. 6 illustrates another embodiment of a secure tote for secure medication transport and administration.

FIG. 6 illustrates another embodiment of a secure tote 600 for secure medication transport and administration. This configuration is also exemplary only, such that other physical configurations may be employed.

In the embodiment illustrated in FIG. 6, the secure tote 600 comprises a securable receptacle 110, a retractable strap 120, a display screen 140, and a communications interface 602. In certain embodiments, the secure tote 600 can be a patient-specific secure tote 600 if it is configured to contain medications for a single selected patient.

Figure 7:
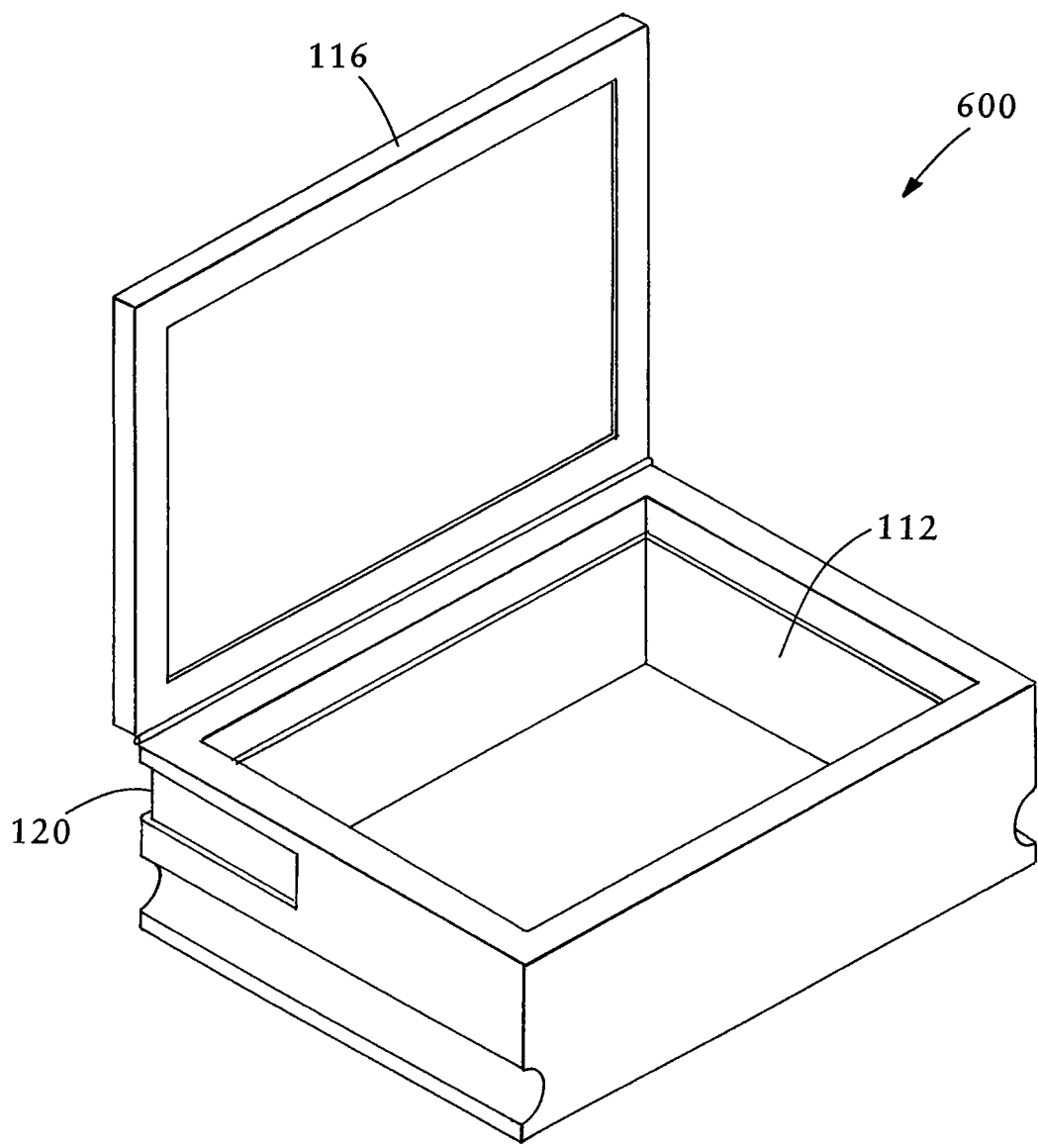
FIG. 7 illustrates the secure tote embodiment of FIG. 6 with an open lid.

The receptacle 110 is configured to be moveable between a closed position, as illustrated in FIG. 6, and an open position, as illustrated in FIG. 7. The receptacle 110 has a plurality of sidewalls that define a storage compartment, as well as a top 116 that is opened and closed about a hinge. A latch assembly can be formed between top 116 and one of the sidewalls to keep top 116 in a closed position until an authorized caregiver gains access to the receptacle 110. The modular receptacle 110 may be used to contain various items.

The secure tote 600 illustrated includes an LCD display screen 140 which can be used to display information such as, but not limited to, access information, patient information and security information. Although an LCD display screen 140 is illustrated, other types of output devices can be used.

The secure tote 600 also features a communications interface 602, represented by a USB female port. Although a USB port is illustrated, other types of communications interfaces can be used. Through the use of a communications module 166 (illustrated in phantom), the communications module 602 is configured to be an interface for transmitting, receiving, and otherwise communicating information with network 180 and/or devices on the network 180, such as the docking station 800 illustrated in FIG. 8.

In certain embodiments, the features, configurations, and uses, including variations, of the secure tote 600 are the same as or similar to the features and configurations of the secure tote 100 discussed above.

Figure 8:
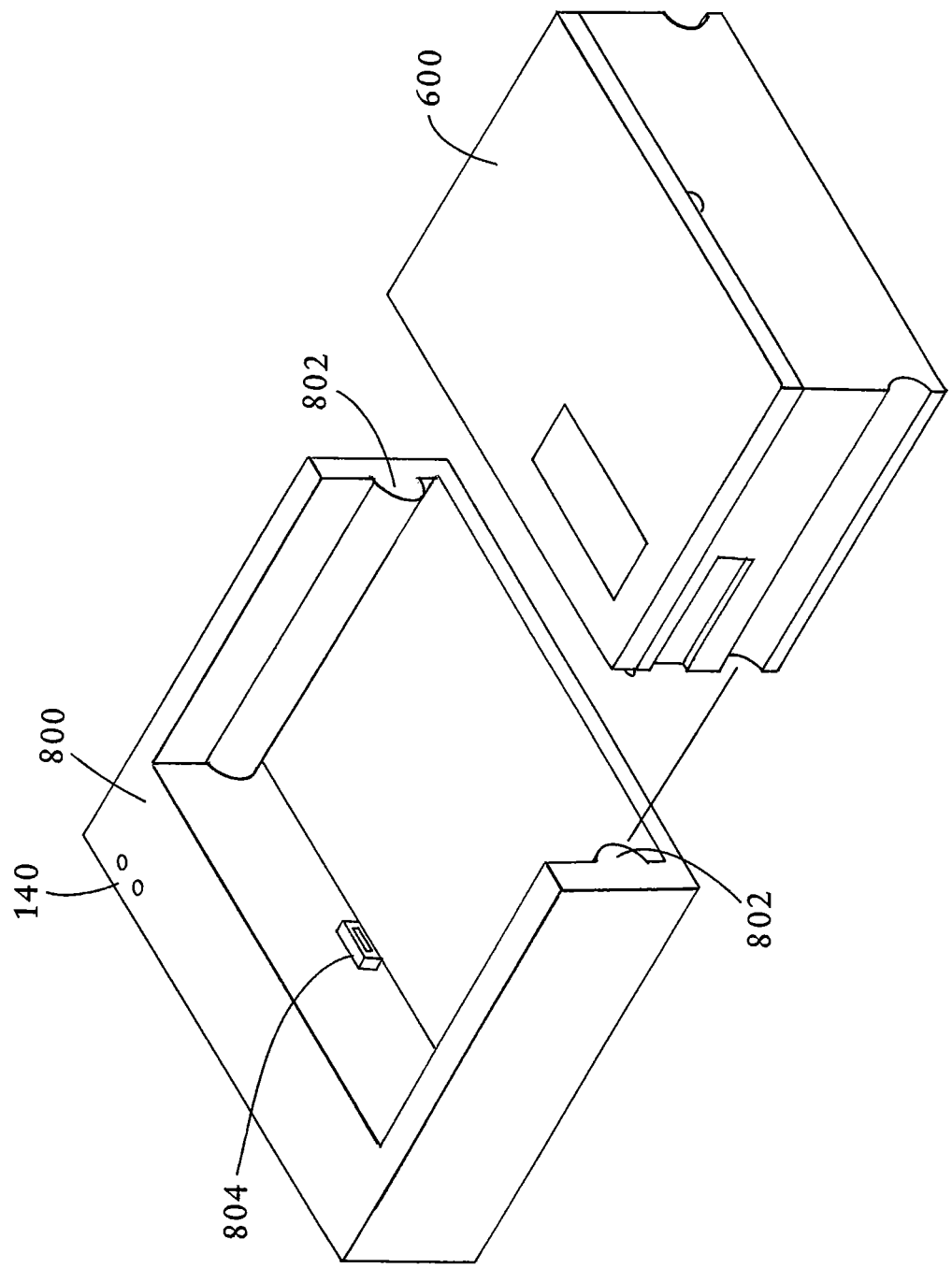
FIG. 8 illustrates a docking station for the secure tote embodiment of FIG. 6.

FIG. 8 illustrates a docking station 800 for the secure tote embodiment of FIG. 6. This configuration is also exemplary only, such that other physical configurations may be employed.

The docking station 800 features a communications module 804, represented by a USB male connector. The USB male connector is configured to connect to the USB female connector of the secure tote embodiment 600 illustrated in FIG. 6. Although a USB connector is illustrated, other types of communications interfaces can be used. The communications module 804 of the docking station 800, using a communications module 166 (not illustrated), is configured to be an interface for transmitting, receiving, and otherwise communicating information with network 180 and/or devices on the network 180, such as the secure tote 600.

The docking station 800 includes indicator lights 140 to indicate a status of the docking station 800. The docking station 800 can also include grooves 802 or other guiding mechanisms to facilitate precisely fitting the secure tote 600 to dock with the docking station 800.

Figure 9:
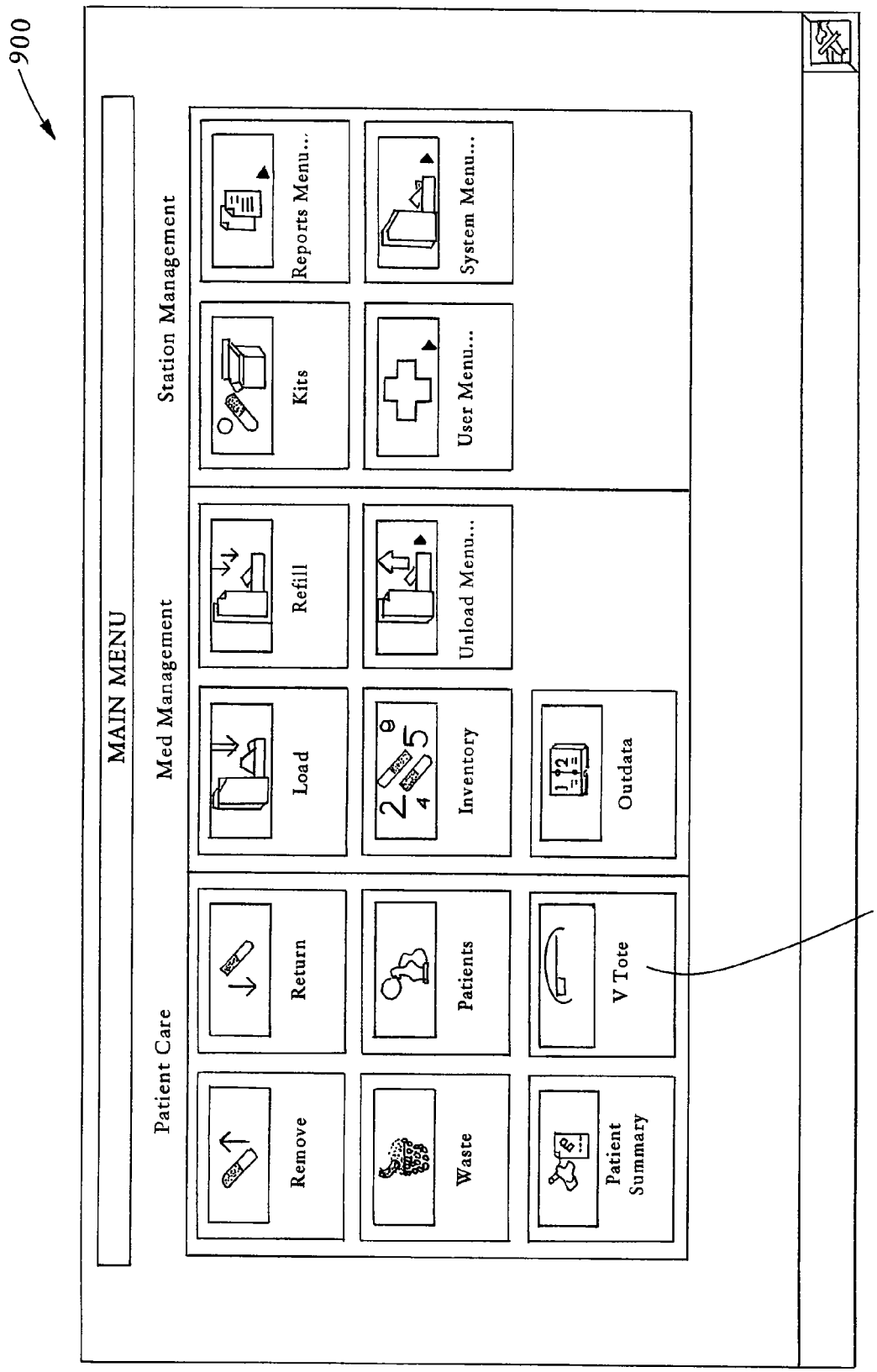
FIG. 9 illustrates a sample screenshot of ADM interface software displaying a docked secure tote.
Figure 10:
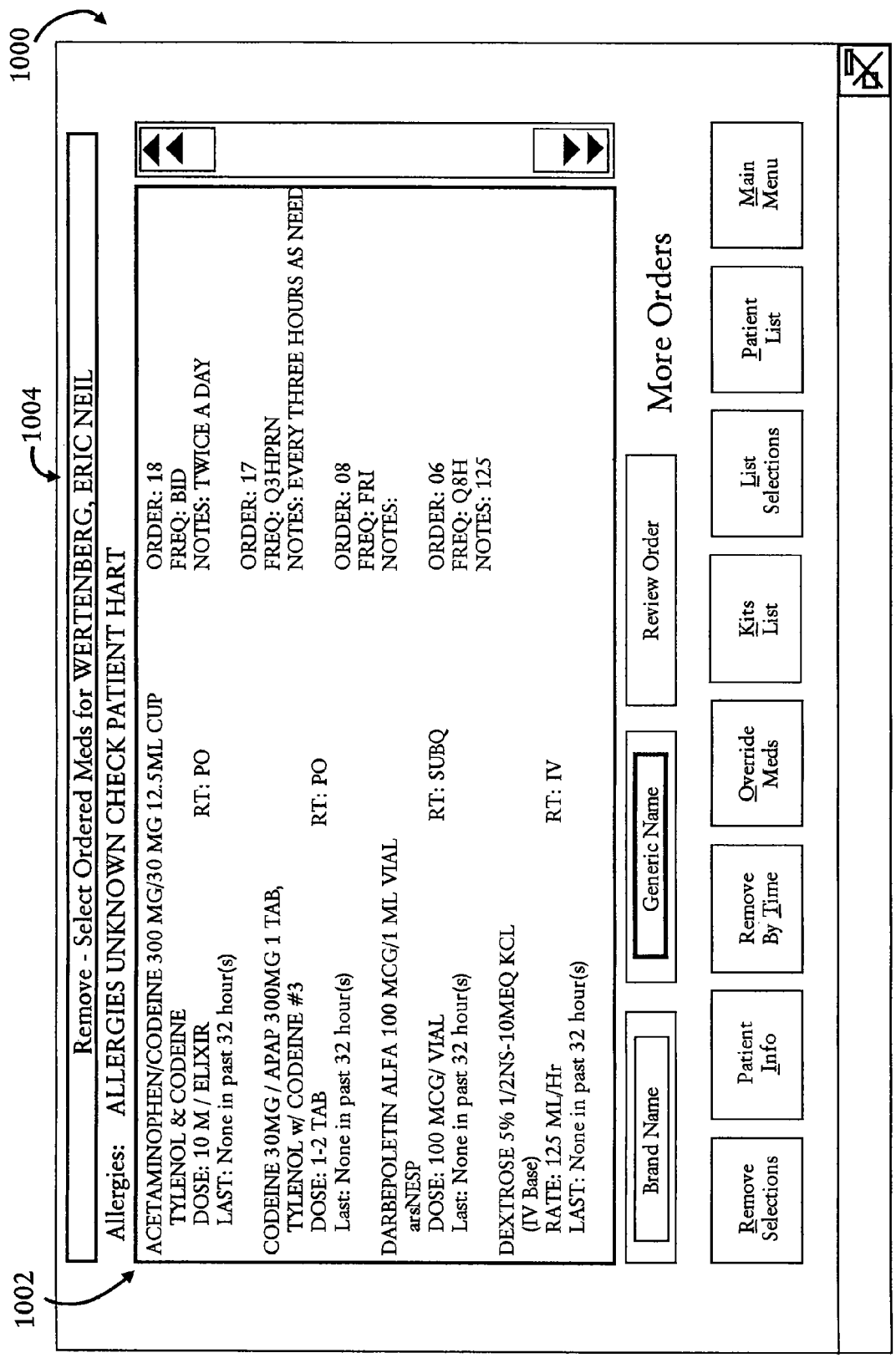
FIG. 10 illustrates a sample screenshot of ADM interface software displaying an assigning of patient-specific medications to a secure tote.

FIG. 9 illustrates a sample screenshot 900 of ADM interface software displaying a docked secure tote. The screen 900 includes a button 902 for accessing information related to the docked secure tote. FIG. 10 illustrates a sample screenshot 1000 of ADM interface software displaying an assignment of patient-specific medications to a secure tote. The screen 1000 includes information on the patient 1004 as well as the medications 1002 for the patient assigned to the secure tote.

Embodiments of the secure tote described herein can be integrated into a facility for use therein according to the different levels of automation available at the facility. For example, in a hospital without ADM automation, use of the secure tote in a pharmacy can comprise (1) filling, via a traditional cart fill type process in the pharmacy, the secure tote with medications for a specific patient, (2) delivering the secure tote to the nurse docking station, and, after the secure tote has been used to dispense medications to the patient, (3) returning the secure tote, which may contain unused items, to the pharmacy. At this final step, the secure tote may be swapped for another secure tote containing medications for the patient, for the next scheduled delivery of medications to the patient.

Use of the secure tote to dispense medications to a patient in a hospital without ADM automation can comprise (1) successfully logging on to a bedside verification system ("BVS"), (2) unlocking the secure tote, (3) dispensing the medications to the patient, and (4) locking the secure tote when completed.

In certain embodiments, in a facility without ADM automation, the secure tote can be used without interacting with any other devices, but may instead function as a stand-alone secure transport for medication, as discussed above.

In a hospital with either basic or advanced ADM automation (i.e., automated filling of the secure tote may be available), similar processes may be used. For example, use of the secure tote in a pharmacy may comprise the additional step of (4) refilling the ADM responsible for filling the secure tote with patient-specific medication. Likewise, use of the secure tote to dispense medications may comprise the additional step of (5) filling the secure tote using the ADM, if available.

In certain embodiments, in a facility with basic ADM automation, the secure tote may store information regarding what patient-specific medications it contains and communicate this information to other devices on the network 180, as discussed above. In certain embodiments, in a facility with advanced ADM automation, the secure tote may further store, communicate, and integrate user information, usage information, and access information, as discussed above.

Although the secure tote 100 has been described and illustrated in examples relating to the transport of medications from an ADM to a patient's bedside, the secure tote 100 has applicability to a broad range of other secure transport and administration uses. For example, the secure tote 100 can be used to transfer medications from a pharmacy to an ADM. The medications could be loaded at a pharmacy into the secure tote 100 by a pharmacist or pharmacy technician and transported to a nurse unit housing the ADM, while implementing the relevant access, logging, and communication features described above.

It should be appreciated from the foregoing description that while certain embodiments of the present disclosure are useful in the medical drug and supply field, other embodiments have applicability to a broad range of industries apart from the medical industry, where similar inventory control and security measures are preferred. The present disclosure is not intended to be limited to the medical supply and drug industry.

While certain aspects and embodiments of the invention have been described, these have been presented by way of example only, and are not intended to limit the scope of the invention. Indeed, the novel methods and systems described herein may be embodied in a variety of other forms without departing from the spirit thereof. The accompanying claims and their equivalents are intended to cover such forms or modifications as would fall within the scope and spirit of the invention.

What is claimed is:
1. A portable medication dispensing system comprising:
a portable medication tote, configured to be carried by a user, comprising:
a plurality of securable compartments, each configured to hold medication;
a controller, responsive to access information comprising patient identification information, user identification information, and an authorized location, the controller configured to:
assign a patient to at least one of the plurality of securable compartments such that medications for the patient are authorized for placement into the at least one securable compartment;
selectively permit the user access to the medications for the patient in the at least one securable compartment by sending a first command to unlock the at least one securable compartment when the access information indicates the user has access to the at least one securable compartment;
restrict access to retrieval of the medications for the patient in the at least one securable compartment by sending a second command to lock the at least one securable compartment when the access information indicates the user does not have access to the at least one securable compartment;

generate an alert if the portable medication tote leaves the authorized location; and store user information, the user information including an assigned caregiver authorized to fill the at least one securable compartment, usage information, and access information for the at least one securable compartment; and an information output module configured to:

output the usage information indicating access to the at least one securable compartment.

2. The system of claim 1, further comprising a communication module configured to transmit the usage information to an information storage device.

3. The system of claim 1, further comprising a communication module configured to communicate with an information storage device.

4. The system of claim 1, further comprising an information storage device configured to store the usage information.

5. The system of claim 1, wherein the usage information comprises at least one of a time value, a communication status, a user identification, a patient identification, an information storage device identification, a medication data, a current status, a usage history, or a configuration.

6. The system of claim 1, wherein the information output module is further configured to provide information regarding the location of the portable medication tote.

7. The system of claim 1, wherein the portable medication tote further comprises an input device.

8. The system of claim 7, wherein the input device comprises at least one of a barcode reader, a keyboard, a touchscreen display, a mouse, a microphone, a magnetic card reader, a biometric reader-sensor, a proximity reader, a radio frequency identification reader, or a symbology reader.

9. The system of claim 1, wherein the portable medication tote further comprises an output device.

10. The system of claim 9, wherein the output device comprises at least one of an audio speaker, a light emitting diode, a cathode ray tube display, a vacuum fluorescent display, a light emitting diode display, a plasma display panel, a liquid crystal display, an organic light emitting diode, or a surface-conduction electron-emitter display.

11. The system of claim 9, wherein the output device is configured to indicate a status of at least one of the controller and the information output module.

12. The system of claim 1, wherein the at least one securable compartment comprises:

a receptacle having a top adapted for movement between an open position and a closed position; and a latch, in association with the top, adapted to be actuated by the controller;

wherein selectively permitting the user access to the medications for the patient in the at least one securable compartment comprises the controller opening the top by actuating the latch when the access information indicates the user has access to the at least one securable compartment.

13. A method, for patient-specific medication dispensing, comprising:

assigning, by a controller, a patient to at least one of a plurality of securable compartments in a portable medication tote, the tote configured to be carried by a user and comprising the controller, the at least one securable compartment configured to store medications for the patient;

selectively permitting, by the controller, access to the user to store the medications for the patient in the at least one securable compartment by sending a first command to unlock the at least one securable compartment when access information indicates the user has storage access to the at least one securable compartment;

comparing a bedside identification of the user and a bedside identification of the patient to the access information to determine whether the user has access to dispense to the patient the medications for the patient in the at least one securable compartment;

selectively permitting, by the controller, access to the user to dispense to the patient the medications for the patient in the at least one securable compartment using the determination;

restricting, by the controller, access to the user to store the medications for the patient in the at least one securable compartment by sending a second command to lock the at least one securable compartment when the access information indicates the user does not have storage access to the at least one securable compartment;

storing user information, the user information including an assigned caregiver authorized to fill the at least one securable compartment, usage information, and access information for the at least one securable compartment;

generating an alert if the portable medication tote is removed from an authorized usage area; and outputting the usage information indicating the user access to the at least one securable compartment, wherein the access information comprises patient identification information, user identification information, and the authorized usage area.

14. The method of claim 13, further comprising restricting access, by the controller, to the user to dispense the medications for the patient in the at least one securable compartment when the access information indicates the user does not have access to dispense the medications in the at least one securable compartment to the patient.

15. The method of claim 13, further comprising recording the output usage information in an information storage device.

16. The method of claim 13, further comprising docking the portable medication tote to a medication storage device storing the medications for the patient before assigning the patient to the at least one securable compartment.

17. The method of claim 13, wherein the bedside identification comprises a barcode, a magnetic strip, or a radio frequency identification.

18. A computer-readable medium having computer-executable instructions for causing a processor to execute instructions to control a portable medication dispensing system by performing steps comprising:

assigning, by a controller, a patient to at least one of a plurality of securable compartments in a portable medication tote, the tote configured to be carried by a user and comprising the controller, the at least one securable compartment configured to store medications for the patient;

selectively permitting, by the controller, access to the user to store the medications for the patient in the at least one securable compartment by sending a first command to unlock the at least one securable compartment when access information indicates the user has storage access to the at least one securable compartment;

restricting, by the controller, access to the user to store the medications for the patient in the at least one securable compartment by sending a second command to lock the at least one securable compartment when the access information indicates the user does not have storage access to the at least one securable compartment;

comparing a bedside identification of the user and a bedside identification of the patient to the access information to determine whether the user has access to dispense to the patient the medications for the patient in the at least one securable compartment;

selectively permitting, by the controller, access to the user to dispense to the patient the medications for the patient in the at least one securable compartment using the determination;

storing user information, the user information including an assigned caregiver authorized to fill the at least one securable compartment, usage information, and access information for the at least one securable component;

generating an alert if the portable medication tote leaves the authorized location; and outputting usage information regarding the user access to the assignment, access, and/or determination made regarding the at least one securable compartment, wherein the access information comprises patient identification information, user identification information, and the authorized location.

19. The computer-readable medium of claim 18, having further computer-executable instructions for performing the step of recording the output usage information in an information storage device.

20. A portable dispensing system comprising:
a portable item tote, configured to be carried by a user, comprising:
a plurality of securable compartments, each configured to hold items;

a controller, responsive to access information comprising patient identification information, user identification information, and an authorized usage area, the controller configured to:

assign an assignee to at least one of the plurality of securable compartments such that items for the assignee are authorized for placement into the at least one securable compartment;

selectively permit the user access to the items for the assignee in the at least one securable compartment by sending a first command to unlock the at least one securable compartment when the access information indicates the user has access to the at least one securable compartment; and restrict access to retrieval of the items for the assignee in the at least one securable compartment by sending a second command to lock the at least one securable compartment when the access information indicates the user does not have access to the at least one securable compartment;

store user information, the user information including an assigned caregiver authorized to fill the at least one securable compartment, usage information, and access information for the patient in the at least one securable compartment;

generate an alert if the portable medication tote is removed from the authorized usage area; and an information output module configured to:
output usage information regarding access to the at least one securable compartment.

* * * * *